US012778770B2

(12) United States Patent
Cowan et al.

(10) Patent No.: US 12,778,770 B2

(45) Date of Patent: *Nov. 3, 2026

(54) INSTRUMENT AND METHOD TO DETERMINE AN INTERVERTEBRAL LOAD

(71) Applicant: Acuity Surgical Devices LLC, Irving, TX (US)

(72) Inventors: Bryan M. Cowan, Dallas, TX (US); John R. Davidson, Westlake, TX (US); Charles R. Forton, Celina, TX (US); Braeley M. George, Dallas, TX (US); Joseph L. Turner, Murphy, TX (US)

(73) Assignee: Acuity Surgical Devices, LLC, Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/967,622

(22) Filed: Dec. 3, 2024

(65) Prior Publication Data

US 2025/0186226 A1 Jun. 12, 2025

Related U.S. Application Data

(63) Continuation of application No. 18/418,205, filed on Jan. 19, 2024, now Pat. No. 12,156,821.

(Continued)

(51) Int. Cl.

*A61F 2/46* (2006.01)
*A61F 2/44* (2006.01)

(Continued)

(52) U.S. Cl.

CPC .......... *A61F 2/4611* (2013.01); *A61F 2/4455* (2013.01); *A61F 2002/2835* (2013.01);

(Continued)

(58) Field of Classification Search

CPC .......... A61B 5/4566; A61B 2562/0261; A61B 2090/064; A61B 2090/065;

(Continued)

(56) References Cited

U.S. PATENT DOCUMENTS

| | | | |
|---|---|---|---|
| 5,197,488 | A | 3/1993 | Kovacevic |
| 7,637,952 | B2 | 12/2009 | Landry et al. |

(Continued)

FOREIGN PATENT DOCUMENTS

| | | | |
|---|---|---|---|
| EP | 3838165 | A1 | 6/2021 |
| EP | 3772350 | B1 | 8/2022 |

OTHER PUBLICATIONS

Patent Cooperation Treaty, International Search Report and Written Opinion issued for PCT Application No. PCT/US2024/012287, dated Apr. 15, 2024, 9 pages.

*Primary Examiner* — Anu Ramana

(74) *Attorney, Agent, or Firm* — Norton Rose Fulbright US LLP

(57) ABSTRACT

Embodiments provide an adjustable cage template for determining a cage for use in a spinal surgery. The adjustable cage template may include top and bottom cage template, control supports. A configuration of the cage template may be modified and sensors may measure forces applied to the cage template during the modification of the cage template configuration. Modifications to the cage template include rotation of the top cage template relative to the bottom cage template, vertical translation of the top cage template relative to the bottom cage template, or both rotation and vertical translation of the top and bottom cage templates. Information associated with measurements from the sensors may be output to determine whether a current configuration (Continued)

of the cage template is optimal and a final cage template may be selected for the spinal surgery based at least in part on the output information.

17 Claims, 8 Drawing Sheets

Related U.S. Application Data

(60) Provisional application No. 63/440,183, filed on Jan. 20, 2023.

(51) Int. Cl.
*A61F 2/28* (2006.01)
*A61F 2/30* (2006.01)

(52) U.S. Cl.
CPC ............... *A61F 2002/30963* (2013.01); *A61F 2002/4658* (2013.01); *A61F 2002/4666* (2013.01)

(58) Field of Classification Search
CPC ............. A61B 2090/067; A61F 2/4611; A61F 2002/4666; A61F 2/76; A61F 2002/7635
See application file for complete search history.

(56) References Cited

U.S. PATENT DOCUMENTS

| | | | | |
|---|---|---|---|---|
| 7,794,499 | B2 | 9/2010 | Navarro et al. | |
| 9,820,869 | B2 * | 11/2017 | Aryan | A61F 2/4657 |
| 9,839,374 | B2 | 12/2017 | Roche et al. | |
| 9,937,055 | B1 * | 4/2018 | Bernhardt, Jr. | A61F 2/4684 |
| 10,524,925 | B2 * | 1/2020 | Bernhardt, Jr. | A61F 2/4684 |
| 10,667,927 | B2 * | 6/2020 | Lamborne | A61F 2/4425 |
| 10,709,574 | B2 | 7/2020 | McLuen et al. | |
| 11,135,070 | B2 * | 10/2021 | Ulrich, Jr. | A61F 2/4611 |
| 11,426,286 | B2 * | 8/2022 | Spetzger | A61F 2/442 |
| 11,491,020 | B2 | 11/2022 | Weiman et al. | |
| 11,712,346 | B2 | 8/2023 | Krawiec et al. | |
| 11,911,290 | B2 * | 2/2024 | Ullrich, Jr. | A61F 2/4611 |
| 2007/0270951 | A1 * | 11/2007 | Davis | A61F 2/4455 623/17.11 |
| 2011/0319755 | A1 | 12/2011 | Stein et al. | |
| 2012/0253406 | A1 * | 10/2012 | Bae | A61F 2/4611 606/279 |
| 2015/0202051 | A1 * | 7/2015 | Tanaka | A61F 2/4455 623/17.16 |
| 2019/0083080 | A1 | 3/2019 | D'Lima et al. | |
| 2021/0038408 | A1 | 2/2021 | Permeswaran et al. | |
| 2022/0008221 | A1 | 1/2022 | Zucker et al. | |
| 2022/0395374 | A1 | 12/2022 | David et al. | |
| 2022/0409140 | A1 * | 12/2022 | Cordonnier | G16H 30/40 |
| 2022/0409400 | A1 | 12/2022 | Zucker et al. | |

* cited by examiner

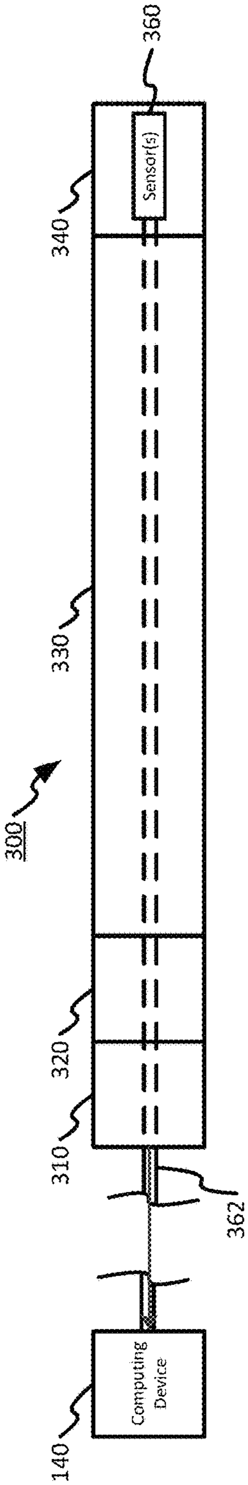
FIG. 3A
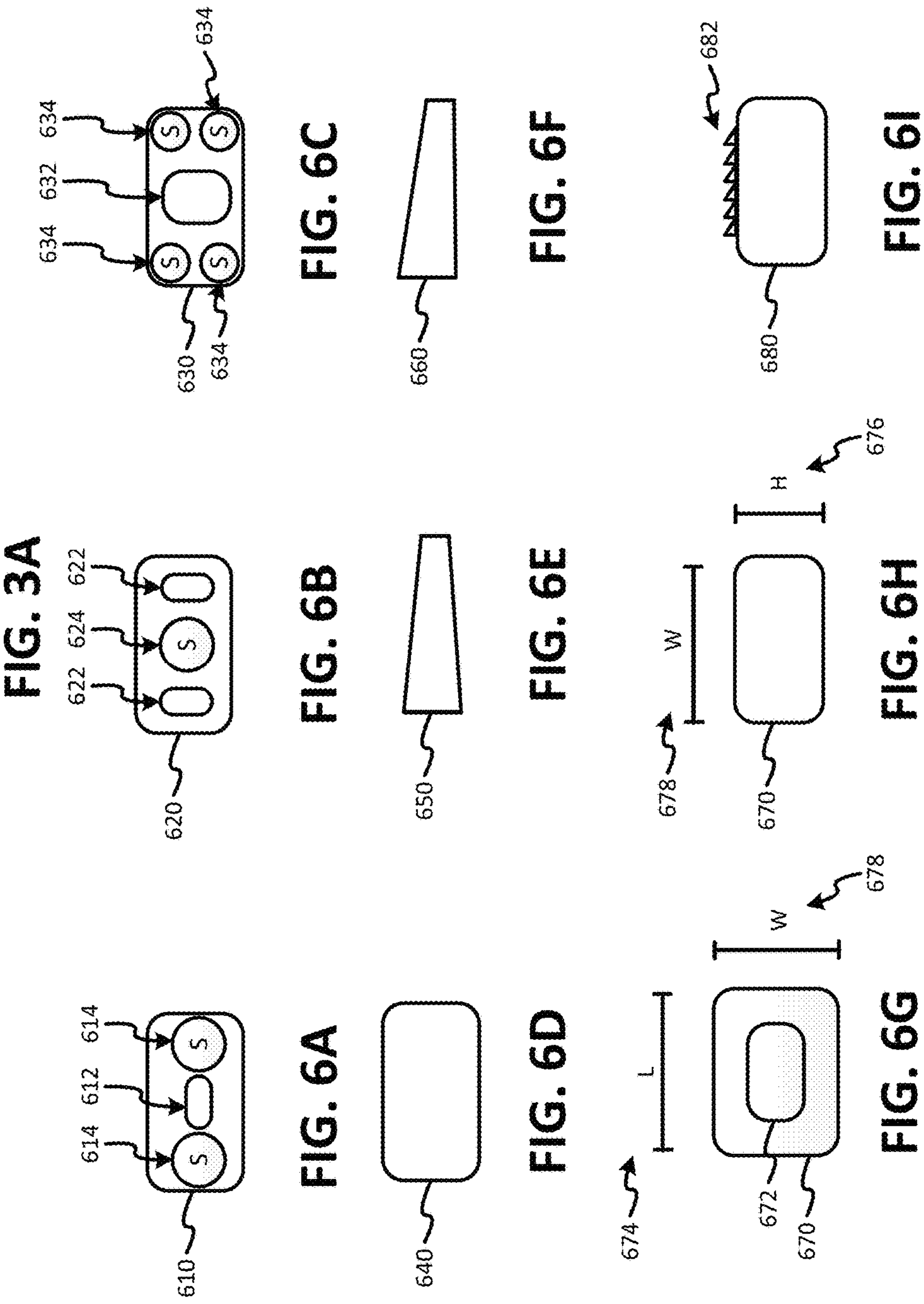
FIG. 6A
FIG. 6B
FIG. 6C
FIG. 6D
FIG. 6E
FIG. 6F
FIG. 6G
FIG. 6H
FIG. 6I

INSTRUMENT AND METHOD TO DETERMINE AN INTERVERTEBRAL LOAD

PRIORITY

The present application is a continuation of U.S. patent application Ser. No. 18/418,205, filed Jan. 19, 2024 and entitled "Instrument and Method to Determine an Intervertebral Load," and issued Dec. 3, 2024 as U.S. Pat. No. 12,156,821, which claims the benefit of U.S. Provisional Patent Application No. 63/440,183, filed Jan. 20, 2023, and entitled "Instrument and Method to Determine Intervertebral Load," the disclosures of which are incorporated herein by reference in their entirety.

TECHNICAL FIELD

The present application discloses systems and methods for performing spinal fusion and more specifically, to systems and methods for determining an intervertebral load in connection with placement of medical devices in the spine.

BACKGROUND

Intervertebral body spacers are commonly used in the spine. For example, intervertebral body spacers, also referred to as cages, are medical devices that may be indicated for intervertebral body fusion of the spine. As an example, these medical devices may be used in skeletally mature patients who have had at least six months of non-operative treatment and are designed for use with allogenic bone graft comprised of cancellous and/or corticocancellous bone graft and/or autograft to facilitate fusion. In practice, one device is used per intervertebral body space. The devices are intended for use at either one level or two contiguous levels in the lumbar spine, from L2 to S1, for the treatment of degenerative disc disease (DDD) with up to Grade I spondylolisthesis. DDD is defined as back pain of discogenic origin with degeneration of the disc confirmed by history and radiographic studies. However, it is noted that intervertebral body space devices may designed for use with other levels of the spine, such as the cervical spine.

Subsidence is a complication resulting from spinal fusion where there is a decrease in the vertical height of the vertebral body space prior to complete fusion (e.g., prior to two levels of the spine or two vertebrae completing fusion). When performing a fusion procedure, surgeons attempt to restore the vertical height through the use of an intervertebral body spacer or cage. However, two forces prevent the complete height from being restored. First, when autograft or allograft bone is used in the disc space to create the fusion, a compressive force is placed on the bone via gravity or the use of posterior fixation to "compress" the vertebral bodies against the bone graft. The bone may remodel under the compressive force due to a concept known as Wolf's Law. Therefore, most surgeons will want the bone graft to have a slight load on it. This loading can reduce the effective vertical height of the operated level. Further subsidence of the intervertebral body cage into the cortical bone at the interface of the cage and the vertebral body may further reduce the effective height, as the bone gives way to the cage, which has harder material properties relative to the adjacent bone structure. Most surgeons accept that this "settling" due to subsidence and graft loading occurs, and any loss in disc space height is compensated for by the rest of the vertebral anatomy as the patient heals. However, too much reduction of height can lead to non-fusion of the bone graft, fracture of the cage, or additional adjacent level vertebral body disease symptoms.

One source of subsidence is "over-distraction" where the surgeon selects an implant through trialing that fits the disc space and restores the proper height. However, presently available procedures for performing such trialing attempt to fit the implant in a manner that applies excessive distraction force to the vertebral body end plates. This occurs due to intentionally choosing an implant larger than the last trial size that fit, or due to the implant having more features than the trial, such as teeth or a roughened porous surface. This causes the surgeon to push the final implant through the endplate, effectively causing subsidence by weakening the underlying bone under too much distraction force. Accordingly, presently available techniques, while capable of achieving insertion of an intervertebral body cage in an appropriate space between two vertebrae, suffer from drawbacks related to subsidence, which may reduce the clinical outcome of the fusion process.

U.S. Pat. No. 9,839,374 (the "'374 Patent"), entitled "System and Method for Vertebral Load and Location Sensing, describes a system for load balance and alignment using a spine instrument having an electronic assembly and sensorized head to report vertebral conditions such as force, pressure, orientation, and edge loading, with a GUI provided to also show the spine instrument position relative to vertebral bodies as the instrument is placed in the inter-vertebral space. However, the '374 Patent does not describe use of the electronic assembly and sensorized head to determine appropriate implant sizing for intervertebral body spacers, such as cages used in spinal fusion.

SUMMARY

Embodiments provide an adjustable cage template for determining a cage for use in a spinal surgery. The adjustable cage template may include top and bottom cage template, control supports. A configuration of the cage template may be modified and sensors may measure forces applied to the cage template during the modification of the cage template configuration. Modifications to the cage template include rotation of the top cage template relative to the bottom cage template, vertical translation of the top cage template relative to the bottom cage template, or both rotation and vertical translation of the top and bottom cage templates. Information associated with measurements from the sensors may be output to determine whether a current configuration of the cage template is optimal and a final cage template may be selected for the spinal surgery based at least in part on the output information.

The foregoing has outlined rather broadly the features and technical advantages of the present invention in order that the detailed description that follows may be better understood. Additional features and advantages will be described hereinafter which form the subject of the claims. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of embodiments described herein, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present embodiments.

BRIEF DESCRIPTION OF THE DRAWINGS

For a more complete understanding, reference is now made to the following descriptions taken in conjunction with the accompanying drawings, in which:

FIG. 3A is a block diagram illustrating an exemplary sizing tool in accordance with aspects of the present disclosure;

FIGS. 6A-6I are block diagrams illustrating additional aspects of cages and cage templates in accordance with aspects of the present disclosure.

DETAILED DESCRIPTION

Figure 1:
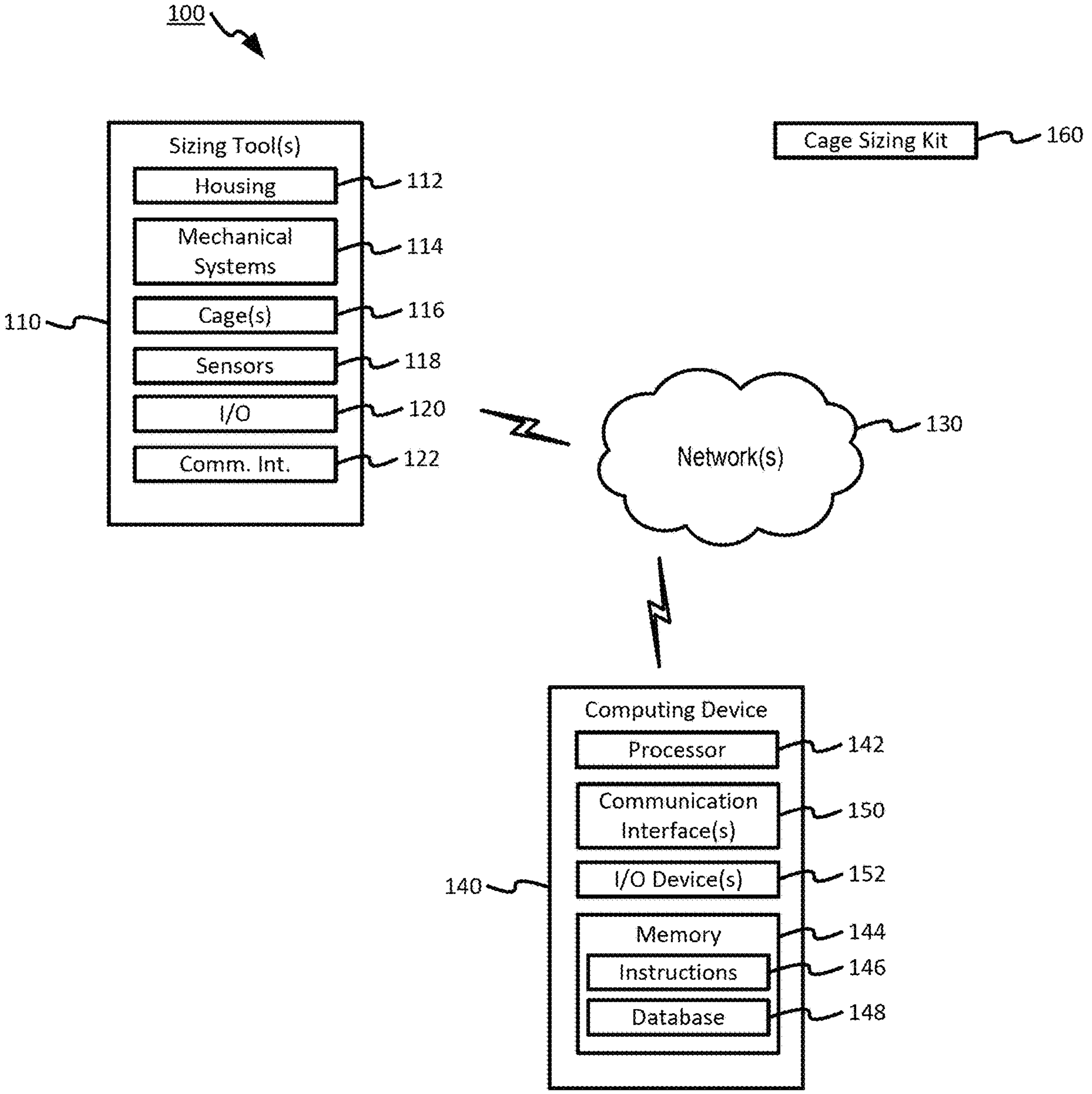
FIG. 1 is a block diagram of a system for determining an optimal cage for a spinal fusion procedure in accordance with aspects of the present disclosure.

Referring to FIG. 1, a block diagram of a system for determining an intervertebral load in connection with placement of medical devices in the spine in accordance with aspects of the present disclosure is shown as a system 100. As will be described in more detail below, the system 100 may be utilized to determine an intervertebral load in connection with placement of medical devices in the spine, such as an optimal cage for use in spinal fusion surgery. The optimal cage may be determined to provide appropriate support across particular bone structures (e.g., harder bone structures instead of soft bone structures) while also being of appropriate dimensions for a space between two different vertebral segments. Exemplary details regarding such optimizations are described in more detail below with reference to FIGS. 2A-6I.

As shown in FIG. 1, the system 100 includes a sizing tool 110 having a housing 112, one or more mechanical systems 114, one or more cages (e.g., one or more intervertebral body spacers or cages), one or more sensors 118, input/output (I/O) devices 120, and one or more communication interfaces 122. The housing 112 may be formed from a metal, such as titanium, aluminum, stainless steel, or another metal suitable for medical applications. In an aspect, the housing 112 may be performed of non-metal materials, such as plastics, suitable for use in medical procedures. It is noted that forming the housing 112 from a metal material may facilitate easier sterilization of the sizing tool 110 (e.g., via autoclaving), but any suitable material capable of being sterilized may be utilized for the housing 112 (or other components of the sizing tool 110). Additionally, or alternatively, the sizing tool 110 may be created as a one-time use device suitable for use in a single surgery and then disposed of.

The mechanical system 114 may be configured to manipulate the one or more cages 116 during a sizing and placement procedure, which may occur prior to performing a spinal fusion. For example, the mechanical systems 114 may include gears, drive shafts, transfer gears, and other mechanisms to rotate, translate, or otherwise move the one or more cages 116 in different positions to determine an optimal cage for a given spine procedure. As an illustrative example of determining an optimal cage for a spinal fusion procedure and referring to FIGS. 2A-2E. In FIGS. 2A-3C, vertebrae segments 202, 204 are shown, each having an intravertebral spacer or cage 222 disposed in a space between the vertebrae segments 202, 204.

Figure 2A:
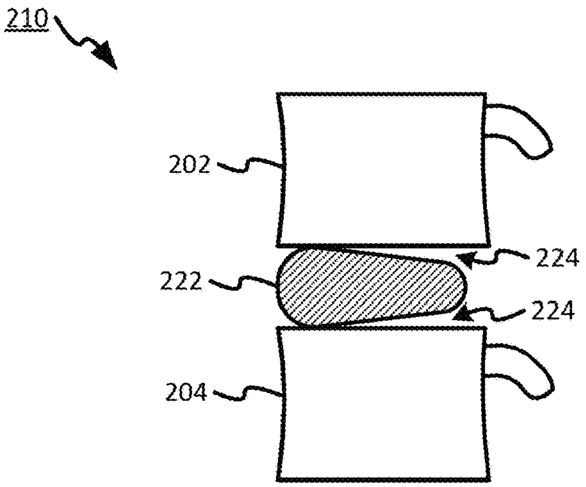
FIGS. 2A-2C are block diagrams illustrating exemplary aspects for determining an optimal cage for a spinal fusion procedure in accordance with aspects of the present disclosure.
Figure 2B:
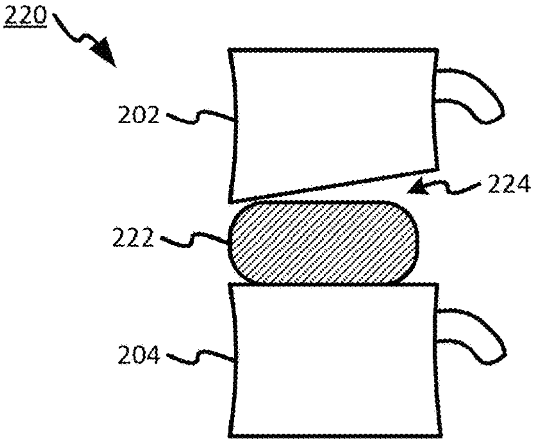
Figure 2C:
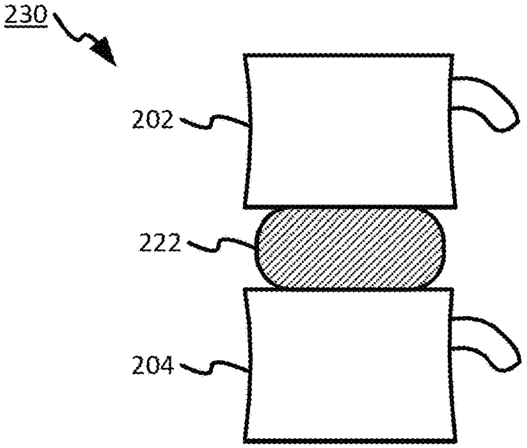

In FIG. 2A it can be seen that the cage 222 is tapered (e.g., from left to right in FIG. 2A) and while portion on the left side of FIG. 2A is appropriately sized (e.g., supporting both the vertebras 202, 204), gaps 224 appear between the tapered end of the cage 222 and the vertebras 202, 204. In such a scenario, subsidence may occur because the two vertebra 202, 204 are not fully supported, leading to improper compressive forces between the vertebras 202, 204 and the cage 222. Stated another way, in FIG. 2A the cage 222 may have a proper height, at least with respect to the leftmost side (in FIG. 2A) of the cage 222, but the cage 222 has an improper lordotic angle, resulting in the spaces 224. Similarly, in FIG. 2B it can be seen that a space 224 exists (on the right side of the drawing) between the cage 222 and the vertebrae 202 due to a lordotic angle mismatch between the bottom of the vertebrae 202 and a top surface of the cage 222. Thus, the cage 222 shown in FIG. 2B is an improperly selected implant due to improper matching of the lordotic angle. In contrast, FIG. 2C shows the cage 222 having a properly selected implant height and lordotic angle, resulting in an optimal cage selection for a particular spine procedure.

As can be appreciated from the foregoing, selection of a properly sized and configured cage can play an important role in the success of a spinal fusion procedure. The sizing tool 110 may be used to determine an appropriately sized and configured cage for a specific spine procedure. For example, the cages 116 may include cages and cage endplates. The cages may correspond to intervertebral devices suitable for use in performing spinal surgeries, such as spinal fusion, and the cage endplates may correspond to measurement devices configured to enable sizing and dimensioning of a vertebral space, which may enable identification of one of the cages that is appropriately sized and dimensioned for the vertebral space at issue during a given medical procedure. For example, a cage endplate may be attached to the sizing tool 110 and manipulated via the mechanical systems 114 to adjust a lordotic angle of the cage endplate to match the lordotic angle of the vertebral space. As an illustrative example, the cage endplates may include a top plate and a bottom plate that may be manipulated via the mechanical systems. Such manipulation may include translating the top and bottom plates away from or towards each other while keeping them parallel or substantially parallel to increase the configured intervertebral height. The manipulation may also include adjusting an angle of the top and/or bottom plates with respect to one another, such as to increase a lordotic angle of the top plate, a lordotic angle of the bottom plate, or both. Exemplary translations and manipulations that may be achieved using the mechanical systems and cage endplates disclosed herein are described in more detail below.

The sensors 118 may be configured to measure a force applied to the cage template by the upper and lower vertebra, which may be used to determine if appropriate compression will be provided for a cage having the size and dimensions of the cage endplate. The sensors 118 may also enable a distribution of the compressive forces to be quantified, such as to determine whether the compressive forces are distributed evenly across a surface of the cage endplate, which may indicate the compressive forces would also be distributed evenly across the surfaces of a cage corresponding to a configuration of the cage endplate. As will be described in more detail below, one or more sensors 118 may include pressure sensors, strain gauges, or other types of sensors configured to measure the forces applied to the cage endplates. In addition to the sensors 118 including sensors configured to measure forces applied to the cage endplates, the sensors 118 may also include other types of sensors, such as sensors configured to measure an amount of force being exerted by the mechanical systems 114 during manipulation of the configuration of the cage endplates.

The I/O devices 120 may provide support for transmitting measurements from the sensors 118 to a remote device, shown in FIG. 1 as a computing device 140. As shown in FIG. 1, the computing device 140 may include one or more processors 142, a memory 144, one or more communication interfaces 150, and one or more I/O devices 152. The memory 144 may include random access memory (RAM) devices, read only memory (ROM) devices, erasable programmable ROM (EPROM), electrically erasable programmable ROM (EEPROM), one or more hard disk drives (HDDs), one or more solid state drives (SSDs), flash memory devices, network accessible storage (NAS) devices, or other memory devices configured to store data in a persistent or non-persistent state. Software configured to facilitate operations and functionality of the computing device 140 may be stored in the memory 144 as instructions 146 that, when executed by the one or more processors 142, cause the one or more processors 142 to perform the operations described herein with respect to the computing device 140, such as to display data obtained by the one or more sensors 118. One or more databases 148 may also be stored at the memory 140. For example, sensor data captured by sensors 118 of the sizing tool may be stored at the database(s) 148. The one or more communication interfaces 150 may be configured to communicatively couple the computing device 140 to the sizing tool 110 via a wired communication link or via a communication link (wired or wireless) via one or more networks 130 via wired or wireless communication links established according to one or more communication protocols or standards (e.g., an Ethernet protocol, a transmission control protocol/internet protocol (TCP/IP), an Institute of Electrical and Electronics Engineers (IEEE) 802.11 protocol, and an IEEE 802.16 protocol, a 3rd Generation (3G) communication standard, a 4th Generation (4G)/long term evolution (LTE) communication standard, a 5th Generation (5G) communication standard, and the like). The one or more I/O devices 152 may include one or more display devices, a keyboard, a stylus, one or more touchscreens, a mouse, a trackpad, a camera, one or more speakers, haptic feedback devices, or other types of devices that enable a user to receive information from or provide information to the computing device 140.

In an aspect, the measurements may be captured by the sensors and transmitted via a set of wires. In an additional or alternative aspect, the measurements may be captured by the sensors 118 and transmitted to the computing device 140 via one or more networks via a wireless communication link.

As an illustrative example, FIG. 3A shows a block diagram illustrating an exemplary sizing tool in accordance with aspects of the present disclosure, shown as sizing tool 300. As shown in FIG. 3A, the sizing tool 300 includes a housing having a main body 330. The main body 300 may include one or more mechanical system interfaces, shown in FIG. 3A as mechanical system interfaces 310, 320. The mechanical system interfaces 310, 320 may be configured to enable manipulation and configuration of cage templates 340 attached to a distal end 340 of the sizing tool 300. As explained above, the cage templates 340 may include sensors 360 that may be communicatively coupled to the computing device 140 via a wired connection or wireless connection. In the example shown in FIG. 3A a wired connection is illustrated, where a wire 362 runs longitudinally through the main body 330 of the sizing tool 300 from sensors 360 to computing device 140. It is noted that one or more extensions or connectors may be utilized to connect the sensors 360 to the computing device 140 if desired, rather than requiring a single continuous wire to be utilized. For example, a portion of the wire 362 may be hardwired inside the main body 330 and a connector may be disposed at the distal end of the sizing tool proximate to where the cage template 340 is coupled to the sizing tool 300. Similarly, a connector may be disposed at a proximal end of the sizing tool 300 to enable a wire or cable to be coupled to the computing device 140. In an additional or alternative aspect, a longitudinal through hole may be provided in which the wire 362 may be passed through and then one or more extensions may be coupled to the wire 362 after existing the proximal end (left side in FIG. 3A) of the sizing tool 300. It is noted that the exemplary configurations described above are provided by way of example, rather than limitation, and other configurations and arrangements may be utilized in accordance with the concepts described herein.

The computing device 140 may be configured to present one or more graphical user interfaces to enable a surgeon to view the sensor data and determine whether an appropriate cage template configuration has been achieved. For example, as explained above, the sensor data captured by the sensor(s) 360 may be used to determine whether pressure or forces are being distributed evenly across the surfaces of the cage template 340. If the forces are not evenly distributed, the one or more mechanical interfaces 310, 320 of the sizing tool 300 may be manipulated to alter a configuration of the cage template 340. As the configuration of the cage template 340 changes, the forces measured by the sensor(s) 360 may change, enabling the surgeon to evaluate different configurations of the cage template 340 to find a configuration that provides an optimal distribution of forces. In another aspect, the computing device 140 may exhibit color coded guidance when excessive pressure or force is measured that indicate a higher risk that a cage placed in that position would lead to subsidence, as described in more detail below. Exemplary configuration modifications and manipulations that may be provided by the one or more mechanical interfaces of the sizing tool in accordance with aspects of the present disclosure are described in more detail below.

Figure 3B:
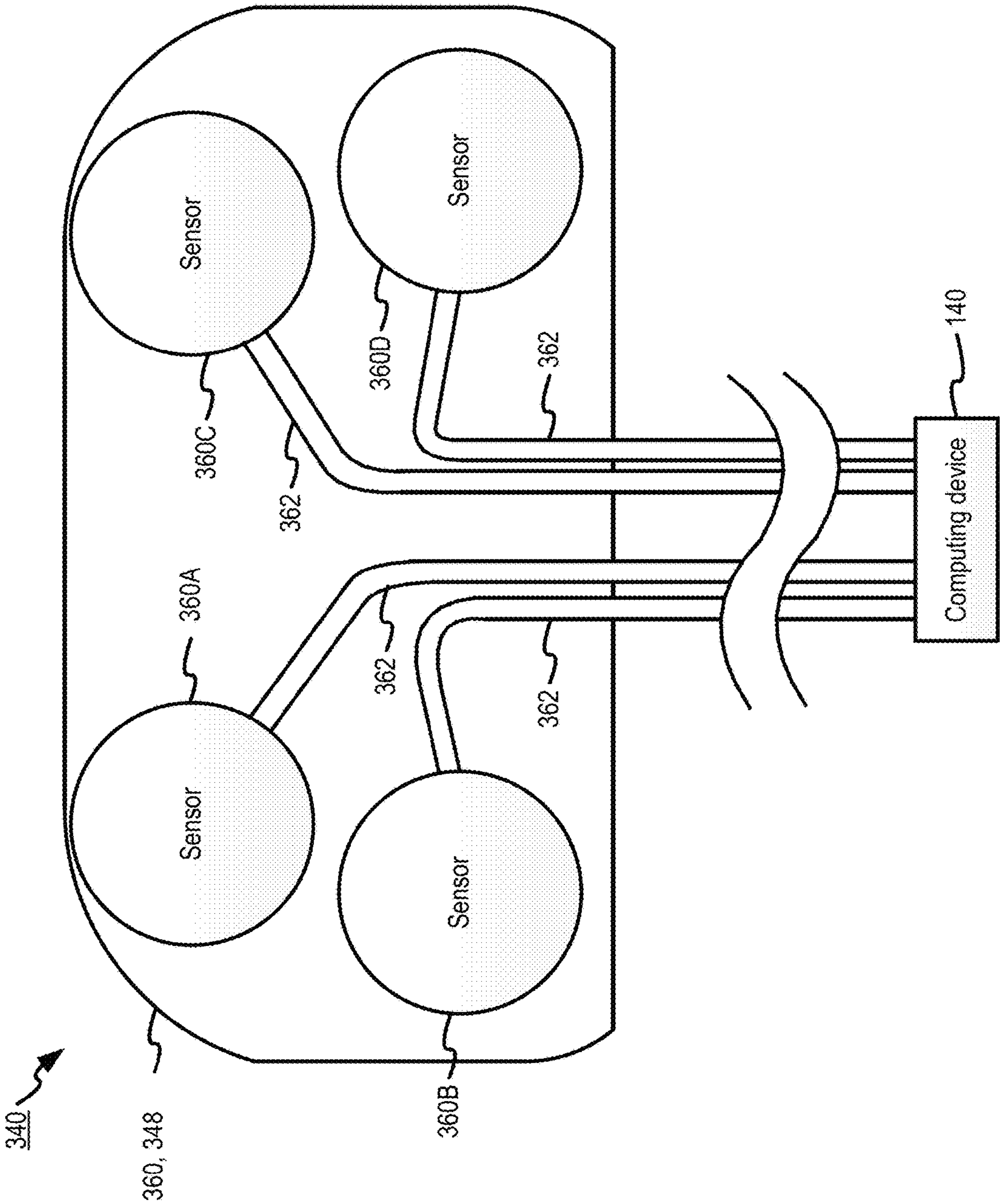
FIGS. 3B-3I are block diagrams illustrating exemplary features of cage templates in accordance with aspects of the present disclosure.

As briefly explained above, the one or more mechanical interfaces 310, 320 may be used to modify a configuration of the cage template. As a non-limiting example, the cage interface 310 may be configured to facilitate translation of a top plate, a bottom plate, or both the top and bottom plates of a cage template. To illustrate, and referring to FIGS. 3B-3H, block diagrams illustrating exemplary features of cage templates in accordance with aspects of the present disclosure are shown. As shown in FIGS. 3C-3F, a cage template in accordance with the present disclosure may include a top cage template 342 and a bottom cage template 348. As shown in FIG. 3B, the top cage template 342 and the bottom cage template 348 may include sensors (e.g., the sensor(s) 360 of FIG. 3A), shown as sensors 360A-360D, located at the peripheral edges of the cage template 340. Locating the sensors along the periphery and near corners of the cage template top and bottom plates may be beneficial as it indicates whether the forces are evenly distributed across the entire surface of the top cage template 342 and the bottom cage template 348. However, it should be noted that other configurations of sensors and cage templates are contemplated herein, as described in more detail with reference to FIGS. 6A-6I. As illustrated in FIG. 4B, the top cage templates and bottom cage template portions may have recessions where the sensors 360A-360D may be placed. The recessions may also include spaces for wires (e.g., the wires 362 of FIGS. 3A, 3B) to be run without being compressed or potentially damaged during alteration of the cage template configuration.

Referring back to FIG. 3C, the top cage template 342 may be supported by a control support 344 and the bottom cage template 348 may be supported by a control support 346. The control supports 344, 346 may be in mechanical communication with one or more mechanical systems 350 (e.g., one or more of the mechanical systems 114 of FIG. 1) and may interface with the one or more mechanical interfaces 310, 320 of the sizing tool 300 to facilitate modification of a configuration of the cage template 340. For example, in FIG. 3D the top cage template 342 and bottom cage template 348 may be translated in the direction indicated by arrow 302 such that the top cage template 342 moves vertically away from bottom cage template 348 and the bottom cage template 348 moves vertically away from top cage template 342. It is noted that the exemplary modification of the cage configuration shown in FIG. 3D may maintain the top cage template 342 and bottom cage template 348 parallel to one another during the translation. However, some alteration in the plates being parallel may occur as compressive forces are applied, such as when the top cage template 342 and bottom cage template 348 reach the relevant vertebra segments and begin to press against them. It is further noted that while described above as translating both the top and bottom cage templates simultaneously, in an aspect, the mechanical systems 350 and the control supports 344, 346 may be configured to restrict translation to only the top cage template 342 or the bottom cage template 348 if desired.

Figures 3C, 3D, 3E, 3F, 3G, 3H, 3I:
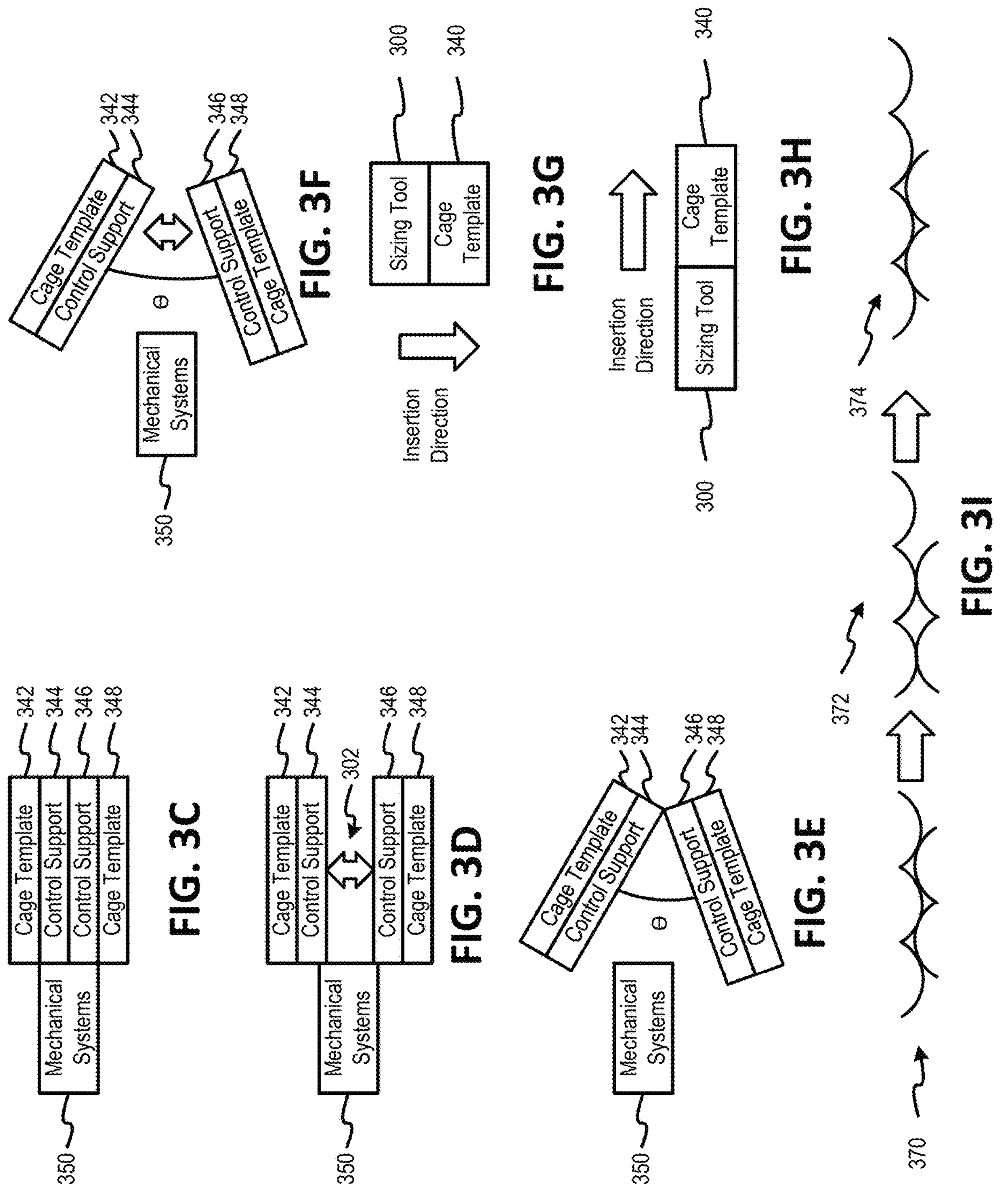
Figure 4B:
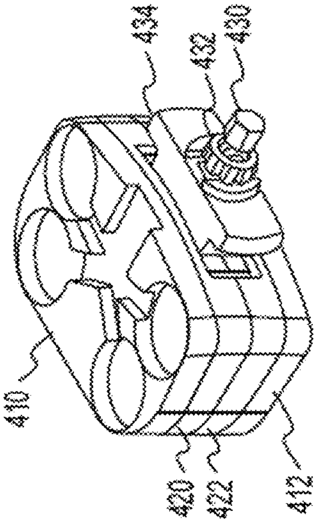
FIGS. 4A-4D are diagrams illustrating various views of a cage template and mechanical interface for performing cage sizing in accordance with aspects of the present disclosure.

In addition to translating the top cage template 342 and bottom cage template 348 as illustrated in FIG. 3D, other types of translations and modifications to the configuration of the cage template 340 may be provided via manipulation mechanical systems of the sizing tool 300 and the cage template(s) (e.g., the mechanical interfaces 310, 320 and the control supports 344, 346). For example, in FIG. 3E a proximal end (left side in FIG. 3E) of the top cage template 242 and the bottom cage template 248 may be pivoted away from each other while distal ends of the top cage template 242 and the bottom cage template 248 remain proximate to each other. As can be appreciated from FIG. 3E, such movement creates an angle (θ) relative to the orientation of the top cage template 342 and bottom cage template 348. In an aspect, the control supports 344, 346 may be configured to restrict the angle (θ), such as to restrict the angle (θ) to be between X° and Y°. In an aspect, the angle (θ) (e.g., the lordotic angle) may between 3 degrees and 30 degrees. In an aspect, the angle (θ) may between 7 degrees and 20 degrees. In an aspect, the angle (θ) may between 5 degrees and 15 degrees. In an aspect, the angle (θ) may between 9 degrees and 22 degrees. In an aspect, cage templates may be limited to a threshold angle range that may be achieved via the concepts described herein. In such instances, multiple cage templates providing different portions of a potential degree range may be provided, such as in 3-5 degree increments, in order to cover all potential ranges for the angle (θ) for a given region of the spine. As in the example of FIG. 3D, while FIG. 3E shows both the top cage template and bottom cage template being moved in response to manipulations of one of the mechanical interfaces 310, 320, in an aspect one of the top and bottom cage plates may remain relatively horizontal and the other may be modified to generate the angle (θ).

As can be appreciated from the exemplary configuration alterations illustrated in FIGS. 3D and 3E, the mechanical systems of the sizing tool (e.g., the mechanical interfaces 310, 320) and corresponding elements of the cage templates (e.g., the mechanical systems 350 and control supports 344, 346) may enable various modifications to the configuration of a cage template. In an aspect, the mechanical interfaces 310, 320 of the sizing tool may correspond to one of the manipulations or configuration changes shown in FIGS. 3D and 3E. For example, the mechanical interface 310 may be configured to effect translation of the top cage template 242 and/or bottom cage template 248 in the manner shown in FIG. 3D, such as by rotating the mechanical interface 310 around a longitudinal axis the main body 330, while the mechanical interface 320 may be configured to effect configuration modification to the top cage template 242 and/or bottom cage template 248 in the manner shown in FIG. 3E, such as by rotating the mechanical interface 320 around a longitudinal axis the main body 330. It is noted that using rotational manipulations of the mechanical interfaces 310, 320 to effect alteration of the configurations cage templates provides a reversible mechanism for determining the optimal cage configuration. For example, if rotation of the mechanical interfaces 310, 320 in a first direction is used to determine the optimal configuration, the mechanical interfaces 310, 320 may be rotated in an opposite direction to reverse the configuration alterations, which may enable the sizing tool and cage template to be more easily removed from the patient. In an aspect, markers may be placed on the exterior surface of the main body 330 or elsewhere on the sizing tool to enable a surgeon to determine a final configuration of the cage template. Once the final configuration is determined, the surgeon may reverse the configuration changes to some extent or completely to remove the sizing tool and cage template and then return the cage template to the final configuration based on the markings noted when the final configuration was identified. This may enable the surgeon to compare the final configuration to one or more cages to identify a cage that matches or is a closest match to the final configuration of the cage template. In an additional or alternative aspect, a table may be provided that includes configuration information based on the markings on the main body 330 (or other portion of the sizing tool) and identifies one or more cage templates providing a closest match to the final configuration information. For example, in Table 1 below, cage configuration information is shown in the left column and includes configurations X of the mechanical interface 310 and configurations Y of the mechanical interface 320. Thus, if the markings when the cage template reaches the final configuration correspond to (X1, Y1), Cage A may be selected from the kit. Similarly, if the markings when the cage template reaches the final configuration correspond to (X2, Y2), Cage B may be selected from the kit, or Cage C may be selected if the markings when the cage template reaches the final configuration correspond to (X3, Y3).

| Configuration Information | Cage |
|---|---|
| Interface 310: $X_1$; Interface 320 $Y_1$ | Cage A |
| Interface 310: $X_2$; Interface 320 $Y_2$ | Cage B |
| Interface 310: $X_3$; Interface 320 $Y_3$ | Cage C |

In an aspect, the mechanical interfaces of a sizing tool in accordance with the concepts described herein may be configured to provide incremental movement of the interfaces used to manipulate the cage configurations, such as to provide a series of slideable teeth as shown in FIG. 3I. As the mechanical interfaces are rotated and transition from state 370 to state 372 and then state 374. When the state 374 is reached, a clicking sound may be generated as the slideable teeth come to rest between opposing teeth. The clicking sound may indicate a single incremental movement has been achieved and the markers on the main body 330 or elsewhere on the sizing tool may be capable of tracking the number of incremental movements made during manipulation of the cage template configuration. For example, in Table 1 above X may correspond to a number of clicks or incremental movements of the mechanical interface 310 and Y may correspond to a number of clicks or incremental movements of the mechanical interface 320. Thus, when Xi, Yi corresponding to the final configuration are known, the surgeon may return the cage template to the final configuration by manipulating the mechanical interfaces 310, 320 to Xi, Yi.

In an aspect, multiple different cage template configuration modifications may be applied simultaneously (e.g., via manipulation of both the interfaces 310, 320), as shown in FIG. 3F, which illustrates translation of the top cage template 342 and bottom cage template 348 as described with reference to FIG. 3D, as well as generation of an angle (θ) as described with reference to FIG. 3E. It is noted that additional translations, modifications, and alterations to the configuration of cage templates may also be provided in accordance with the concepts described herein.

It is noted that the sizing tool 300 may provide similar translations and alterations in different manners depending on the type of cage to be provided and the procedure used to insert the cage. For example, spinal fusion surgery may be performed using a lateral approach (e.g., the cage is inserted through an incision on the side of the patient's torso), an anterior approach (e.g., the cage is inserted through an incision on the front side of the patient's abdomen), or a posterior approach (e.g., the cage is inserted through an incision in the patient's back). For the lateral approach the sizing tool 300 and cage template 340 may be arranged as shown in FIG. 3G, while for the anterior and posterior approaches the sizing tool 300 and cage template 340 may be arranged as shown in FIG. 3H. It is noted that while FIGS. 3G and 3H may appear to merely be rotations of each other, the mechanical systems may be configured differently to provide similar transformations in these two arrangements. For example, in FIG. 3G, the mechanical systems of the sizing tool and cage templates may be configured to produce an angle (θ) in which the top and/or bottom cage templates are pivoted in a manner that is parallel to the insertion direction, similar to what is shown in FIG. 3E except the mechanical systems 350 would be located behind the cage template 340 (in the view of FIG. 3E). In contrast, the angle (θ) may be formed in a manner that is perpendicular to the insertion direction of FIG. 3H when the anterior or posterior approach is utilized. As such, there may be different sizing tools having different mechanical system configurations depending on the type of approach that is utilized to perform a particular spinal fusion surgery.

If a satisfactory configuration for the cage template is determined (e.g., a configuration that distributed the forces evenly across the upper and lower surfaces of the cage template based on the sensor data), the sizing tool 300 and cage template 340 may be removed from the patient's body and a cage having a configuration approximating or equivalent to a final configuration of the cage template may be selected. For example, the sizing tool 300 may be part of a kit that includes a variety cages for implantation in a patient. The cages of the kit may include different lordotic angle configurations, heights, or other features. After identification of the appropriate configuration of the cage template, the cages of the kit may be consulted to identify a cage that matches or most closely approximates the configuration of the cage template following a sizing procedure in accordance with the concepts described herein. Once the appropriate cage is selected, the cage may then be inserted into the space between the vertebra segments of the patient to facilitate spinal fusion. For example, in the exemplary situations shown in FIGS. 2A-2C the selected cage may correspond to the cage 222 shown in FIG. 2C, rather than the cages shown in FIGS. 2A and 2B. If the initial cage template cannot be manipulated to achieve a satisfactory configuration, a different cage template may be selected from among the kit or a new kit may be selected having a different cage template and the above-described configuration procedure may be repeated to determine if a better cage configuration can be identified. If no optimal cage is identified using the sizing procedures described above, a closest fit cage may be selected from the kit(s).

Because a cage that is appropriately sized to facilitate even distribution of the compressive forces is selected based on the sizing and configuration techniques described herein, a likelihood of subsidence may be minimized and which may promote improved spinal fusion. It is also noted that the likelihood of subsidence may also be minimized using other techniques. For example, an initial cage template may be selected based on bone characteristics using the techniques described in PCT/US22/49515, filed Apr. 11, 2023, and entitled "Method and Apparatus for Reducing Human Vertebral Body Subsidence Using Variable Surface Area Interbody Cages Correlated to Localized Bone Density Measurements", the content of which is incorporated herein by reference, which may provide information on candidate cage sizes and shapes that may support and be supported by dense bone of the spinal segments to further reduce a likelihood of subsidence. Accordingly, it should be understood that an initial candidate cage template may be selected based on bone characteristics of the relevant vertebra segments and then the sizing and configuration techniques described herein may be used to determine an optimal configuration of the cage that will ultimately be used in spinal fusion surgery. In an aspect, one or more bone screws may be used to secure the cage in place once inserted into the space between the vertebra segments.

Figure 4D:
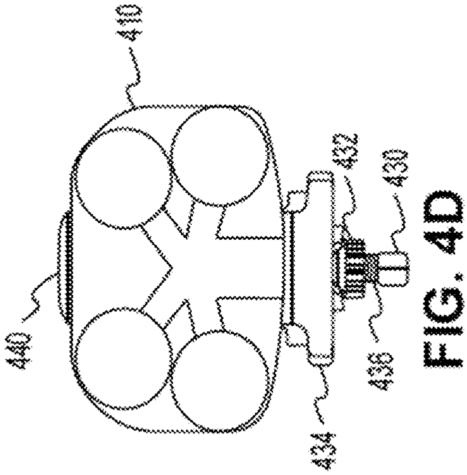
Figure 4A:
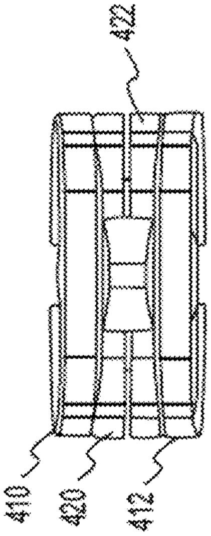
Figure 4C:
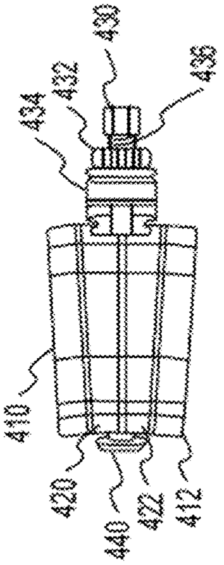

Referring to FIGS. 4A-4D, various views of a cage template and mechanical interface for performing cage sizing in accordance with aspects of the present disclosure are shown. In particular, FIG. 4A shows a front view of a distal end of a cage template in accordance with the present disclosure; FIG. 4B shows a perspective view of a cage template in accordance with the present disclosure; FIG. 4C shows a lateral view of a cage template in accordance with the present disclosure; and FIG. 4D shows a top/bottom view of a cage template in accordance with the present disclosure. As shown in FIGS. 4A-4D, a cage template may include a top cage template 410, a bottom cage template 412, control supports 420, 422, and an expansion housing 440, which may be used to retain the mechanical systems such that they do not disassemble when the cage template is placed in its initial insertion configuration (i.e., shortest and least lordosis). Similarly, the cage template may include mechanical systems 430, 432, 434, 436 configured to interface with mechanical systems of the sizing tool to facilitate manipulation and modification of the cage template. As a non-limiting example, the mechanical systems of the cage template may include a drive shaft 436, a gear 432, and a support member 434. The drive shaft 430 may have a hexagonal head 430 configured to mate with a corresponding interface of the main body of the sizing tool, such as an interface in mechanical communication with one of the mechanical interfaces 310, 320 of FIG. 3A. The drive shaft may be threaded such that rotation of a mechanical interface of the sizing tool main body (e.g., the mechanical interface 310 or 320) causes rotation of the drive shaft 436. The rotation of the drive shaft 436 may cause the gears 432 to rotate, which may interact with the control supports 420, 422 to effect the translations and manipulations of the cage template configurations described above.

Figure 5:
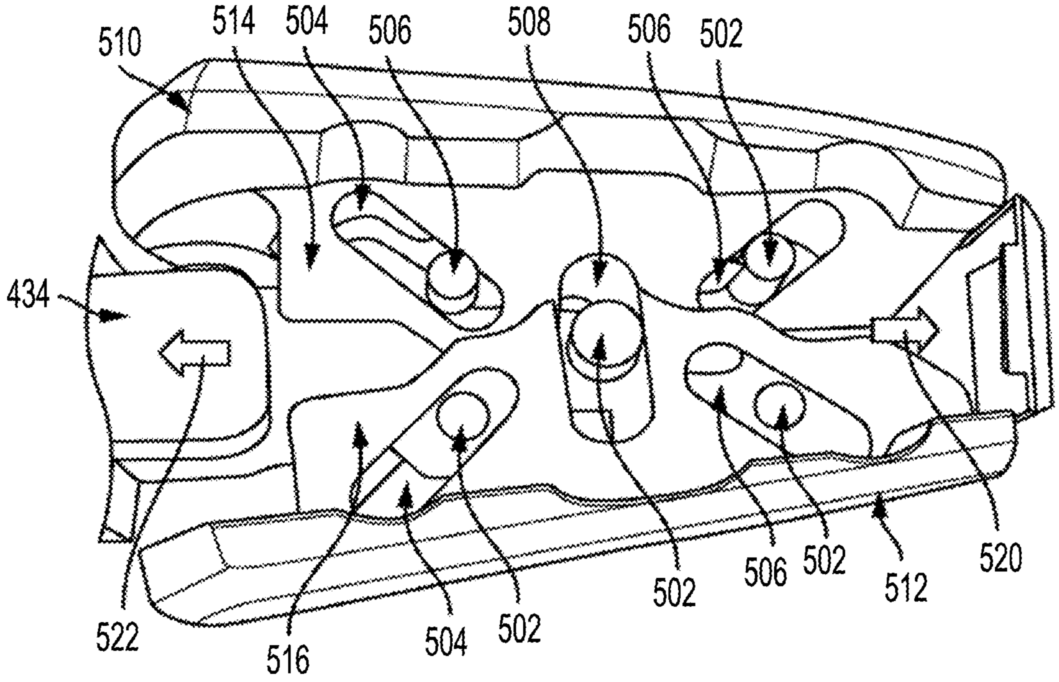
FIG. 5 is an image of a cage template in accordance with aspects of the present disclosure.

To further illustrate the exemplary mechanical systems and mechanisms for effecting the manipulations and transformations of the configuration of the cage template, FIG. 5 shows an image of a cage template in accordance with aspects of the present disclosure. As can be seen in FIG. 5, the cage template includes a top cage template 510 and a bottom cage template 512, and control supports 514, 516. Control supports 514, 516 includes guide slots 504, 506 and a central slot 508, and pins 502 may be positioned within each of the slots 504, 506, 508. As explained above, when the drive shaft 436 is rotated in a first direction, indicated by arrow 520, the top and bottom cage templates 510, 512 may be moved. During such movement, the pins 502 in the slots 504, 506 may control creation of the angle θ, as described above with reference to FIGS. 3E-3F. Similarly, the pin 502 in slot 508 may control translation of the top and bottom cage templates as described above with reference to FIGS. 3D and 3F. Similarly, reversing the direction of rotation in the drive shaft 436 in the direction 522 may reverse the movements of the top and bottom cage templates. In an aspect, as the drive shaft 436 is rotated in the first direction, the support member 434 may be advanced in the direction 520 and reversed in the direction 522 when rotated in the opposite direction. As the support member 434 is advanced, the translations and manipulations of the top and bottom cage plates 510, 512 may be effected, while the guide slots 504, 506, 508 may constrain the range of movement for the translations and manipulations. In an aspect, multiple drive shafts and support members 434 may be provided to effect different types of translations and manipulations of the top and bottom cage plates 510, 512, as described above. For example, a first drive shaft and support member 434 may be configured to control translation of the top and bottom cage plates 510, 512 as described above with reference to FIG. 3D and a second drive shaft and support member 434 may be configured to control creation of the angle θ with respect to the top and bottom cage plates 510, 512 as described above with reference to FIG. 3E.

It is noted that while exemplary details regarding cages and cage templates have been described, it is to be appreciated that such exemplary cages and cage templates have been provided for purposes of illustrating the concepts disclosed herein and that the sizing tools and techniques described herein may be utilized with any of a variety of cages and other medical devices used in spinal surgeries. For example, FIGS. 6A-6I are block diagrams illustrating additional aspects of cages for which the above-described sizing and configuration techniques may be applied. In FIG. 6A, a cage 610 is shown and includes a central aperture 612 and a sensor 614 disposed on either side of the central aperture 612. Similarly, FIG. 6B is a block diagram of a cage 620 having two apertures 622 disposed on longitudinal edges of the cage 620 and a single sensor 624 disposed between the two apertures 622, and FIG. 6C is a block diagram of a cage 630 having a central aperture 632 and 4 sensors 634 disposed on corners of the cage 630. As can be appreciated from FIGS. 6A and 6B, it is to be understood that cage templates according to the present disclosure may utilize one or more sensors to determine an optimal cage configuration, rather than being limited to 4 sensors as described above with reference to FIG. 3B.

Referring to FIGS. 6D-6F, block diagrams illustrating side profiles that may be achieved using the sizing and configuration techniques described herein are illustrated. In particular, FIG. 6D illustrates a cage profile 640 in which the top and bottom cage templates are maintained substantially parallel to each other, FIG. 6E illustrates a cage profile 650 in which the top and bottom cage templates are manipulated to form the angle (θ), and FIG. 6F illustrates a cage profile 660 in which only the top cage template is manipulated to form the angle (θ). As can be appreciated from FIGS. 6D-6F, the manipulations and transformations described above may enable a variety of cage profiles to be created, including via use of multiple transformations simultaneously as described above with reference to FIG. 3F, thereby providing a robust capability to size the appropriate cage for a particular spinal surgery, patient anatomy, and bond characteristics.

Referring to FIGS. 6D and 6H, block diagrams illustrating additional aspects of cage templates in accordance with aspects of the present disclosure are shown. In particular, FIGS. 6G and 6H illustrate a cage template 670 having a central aperture 672. The cage 670 is also shown to have a length 674, a height 676, and a width 678. As explained above, the height 676 of the cage template 670 may be modified, such as to increase or decrease the height 676 using the translations described above with reference to FIG. 3D. Similarly, the height 676 may be adjusted such that the height of the cage template 670 is not uniform via formation of the angle (e) as described above with reference to FIG. 6E. Additionally, the height 676 may be adjusted such that the height of the cage template 670 increases or decreases and is also not uniform via translations described with reference to FIGS. 3D and 3F and formation of the angle (θ) as described above with reference to FIGS. 3E and 3F.

In FIG. 6I, a block diagram of a cage having teeth on at least a top or bottom surface is shown. In particular, FIG. 6I shows a cage 680 having teeth 682 on a top surface. The teeth 682 may be provided to help hold the cage 680 in place and/or promote bone growth of the spinal segments where the cage 680 is inserted. In an aspect, a cage template may be designed to approximate a total height of the cage 680, such as by having a height of the cage template be equal to or approximately equal to the height of the cage 680 taking into account the presence of the teeth 682. However, in such instances, the cage template may not have teeth to facilitate easier insertion and removal of the sizing tool and cage template.

Figure 7:
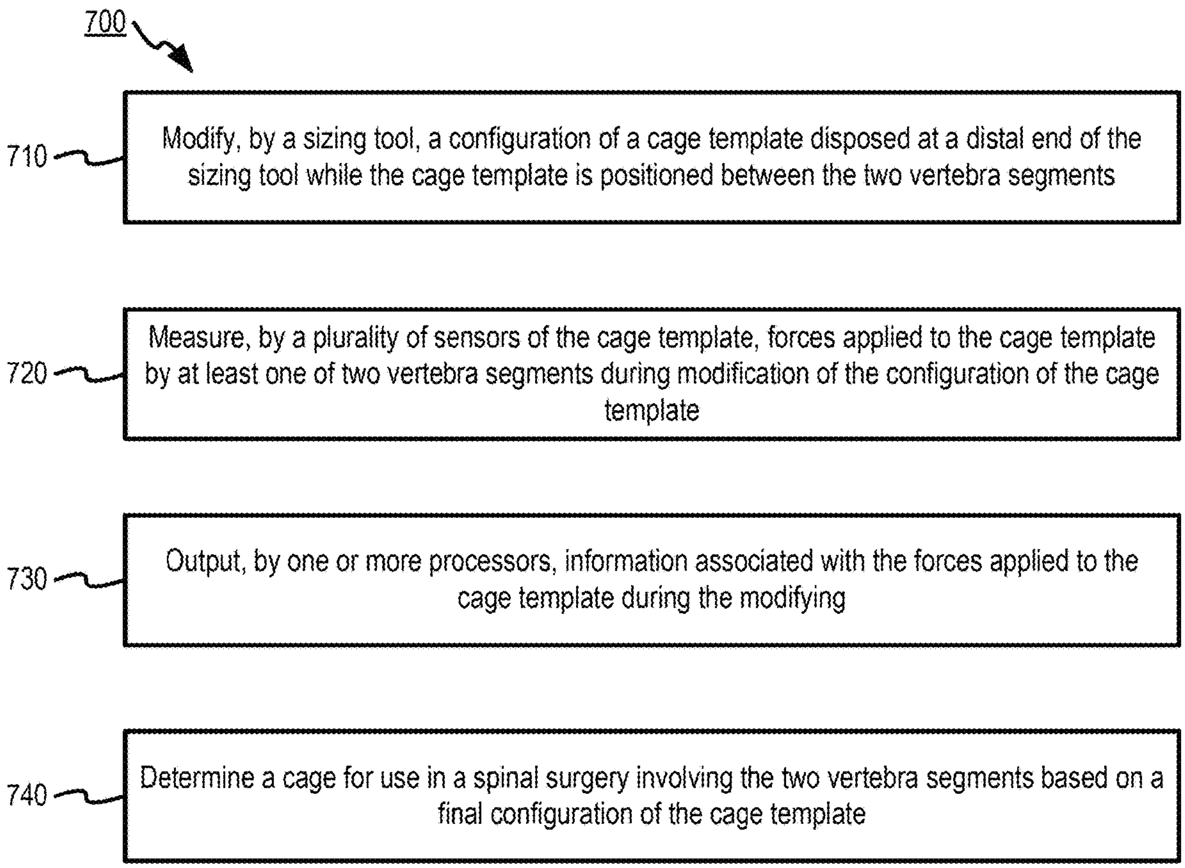
FIG. 7 is a flow diagram of an exemplary method for determining an optimal cage for a spinal fusion procedure in accordance with aspects of the present disclosure in accordance with aspects of the present disclosure.

Referring to FIG. 7, a flow diagram of an exemplary method for determining appropriate implant sizing for a medical implant for use in a spinal surgery involving two vertebra segments si shown as a method 700. As explained above, the medical implant sized using the method 700 may be a cage for spinal fusion surgery. As explained above, the method 700 may be performed using a cage template, such as the exemplary cage templates described above with reference to FIGS. 1-6I, to determine appropriate sizing for the medical implant.

At step 710, the method 700 includes modifying, by a sizing tool, a configuration of a cage template disposed at a distal end of the sizing tool while the cage template is positioned between the two vertebra segments. In an aspect, the cage template may be modified as described above with reference to FIGS. 3C-3F. As explained above, the modifying may be configured to alter a lordotic angle of the cage template, a height of the cage template, or both. In an aspect, modification of the configuration of the cage template may achieved using one or more mechanical interfaces of the sizing tool, such as the mechanical interfaces 310, 320 of FIG. 3A.

At step 720, the method 700 includes measuring, by a plurality of sensors of the cage template, forces applied to the cage template by at least one of two vertebra segments during modification of the configuration of the cage template. In an aspect, the sensors may be embedded in or reside in top and bottom cage templates of the cage template, such as in the recesses shown in FIG. 4B. At step 730, the method 700 includes outputting, by one or more processors, information associated with the forces applied to the cage template during the modifying. As explained above, the sensors of the cage template may be in wired or wireless communication with one or more remote devices, such as the computing device 140 of FIG. 1, and may provide sensor data and measurements to the remote device(s) for display. For example, the computing device may be configured to receive the measurements from the sensors of the cage template and present information associated with the sensors at a display device (e.g., a monitor). For example, the sensor measurements may be displayed as raw data (e.g., force or pressure readings). Additionally or alternatively, information derived from the sensor measurements may be generated by the computing device and displayed. For example, a graphical user interface may display one or more color coded indicators to indicate the pressure or forces being applied to the cage template as the configuration is being adjusted. As a non-limiting example, red may indicate too much pressure or force, yellow may mean caution (e.g., risk of over distraction, etc.), and green may indicate good pressure or force. It is noted that other types of information may be presented to provide real-time feedback regarding the pressure being applied to the cage template during adjustment of the cage template configuration. For example, an image of a cage template may be displayed and color indicators or other information may be presented on the image of the cage template to indicate the pressure or forces being applied to various regions of the cage template (e.g., to indicate portions of the top or bottom cage templates having good pressure, too much pressure, little pressure, etc.).

At step 740, the method 700 includes determining a cage for use in a spinal surgery involving the two vertebra segments based on a final configuration of the cage template. As explained above, based on the measurements from the sensor data and the manipulations of the cage template, a surgeon may be able to determine an optimal cage configuration, which may be a cage that has an appropriate lordotic angle and/or height and results in appropriate force being applied to the cage template. For example, the optimal cage configuration may provide greater force around all or portions of a periphery of the cage template, which may be where stronger or harder bone is located, and some force near the graft window (e.g., the aperture(s) of the cage or cage template). By ensuring stronger forces are observed where harder bone mass is located and less force is present where softer bone mass is located, the risk of subsidence may be reduced or eliminated, which may improve the clinical outcome of the spinal surgery. As explained above, the final configuration of the cage template may be determined based at least in part on the modifying and the information associated with forces applied to the cage template during the modifying. In an aspect, the remote computing device may be configured to display the final configuration of the cage template and/or the optimal cage(s) to be used for the spinal surgery. For example, the computing device may use the sensor measurement data and information associated with the cage template being used to identify the optimal cage (e.g., using a lookup table or another technique).

In an aspect, the method 700 may include selecting a different cage template in response to determining an optimal configuration of the cage template is not achievable using the cage template. In such instances, the modifying, measuring, outputting, determining of steps 710-740 may be repeated with the different cage template. For example, the initial cage template may have a first height range and the different cage template may have a second height range that is greater than or less than the first height range, the first height range corresponding to range of cage template heights achievable with the cage template via the modifying and the second height range corresponding to range of cage template heights achievable with the different cage template via the modifying. If insufficient pressure or force is achieved using an initial cage template, a different cage template having a greater height range may be utilized with the metho 700 to evaluate whether the increased height enables appropriate force or pressure to be achieved. A similar approach may be utilized if the lordotic angle needs to be modified. For example, the initial cage template may have a first lordotic angle range and the different cage template may have a second lordotic angle range that is greater than or less than the first lordotic angle range, the first lordotic angle range corresponding to range of lordotic angles achievable with the cage template via the modifying and the second lordotic angle range corresponding to range of lordotic angles achievable with the different cage template via the modifying. It is noted that in some instances, cages templates having the same height but different lordotic angles may be utilized, such as when the height is correct, but the angle is incorrect for the first cage template.

Clause 1: A cage template mechanically couplable to the distal end of the main body, the cage template comprising: a top cage template; a bottom cage template; a first sensor corresponding to the top cage template; a second sensor corresponding to the bottom cage template; and first and second control supports coupled to the top cage template and the bottom cage template, respectively, where the top cage template and the bottom cage template may be moveable relative to each other to alter a configuration of the cage template. In an aspect, the top cage template and the bottom cage template may be moveable relative to each other to alter a configuration of the cage template as explained above with reference to FIGS. 1-6I.

Clause 2: A system comprising: a cage template mechanically couplable to the distal end of the main body, the cage template comprising: a top cage template; a bottom cage template; a first sensor corresponding to the top cage template; a second sensor corresponding to the bottom cage template; and first and second control supports coupled to the top cage template and the bottom cage template, respectively; and a sizing tool comprising: an elongated main body having a proximate end and a distal end; means for transferring a mechanical force to the first and second control supports to modify a configuration of the cage template while the cage template is disposed between two vertebra segments, wherein the first sensor is configured to measure a first force applied to the top cage template by at least one of two vertebra segments during modification of the configuration of the cage template and the second sensor is configured to measure a second force applied to the bottom cage template by at least one of two vertebra segments during modification of the configuration of the cage template; and means for outputting the first force and the second.

Clause 3: The system of clause 1, wherein the cage template comprises an aperture corresponding to a graft window.

Clause 4: The system of clause 1, wherein the cage template comprises a third sensor corresponding to the top cage template, and wherein the first sensor and the third sensor are disposed on opposite sides of an aperture of the cage template.

Clause 5: The system of clause 3, wherein the cage template comprises a fourth sensor corresponding to the bottom cage template, and wherein the second sensor and the fourth sensor are disposed on opposite sides of the aperture of the cage template.

Clause 6: The system of clause 1, further comprising a plurality of additional sensors, wherein the plurality of additional sensors includes a first set of sensors corresponding to the top cage template and a second set of sensors corresponding to the bottom cage template, the first set of sensors comprising sensors disposed about a periphery of the top cage template and the second set of sensors comprising sensors disposed about a periphery of the bottom cage template.

Clause 7: The system of clause 5, wherein the plurality of additional sensors includes a third set of sensors corresponding to the top cage template and a fourth set of sensors corresponding to the bottom cage template, the third set of sensors comprising sensors disposed about a central aperture of the cage template and the fourth set of sensors comprising sensors disposed about a central aperture of the cage template.

Clause 8: The system of clause 1, wherein modification of the configuration of the cage template comprises translating the top cage template vertically relative to the bottom cage template.

Clause 9: The system of clause 1, wherein modification of the configuration of the cage template comprises rotating the top cage template vertically relative to the bottom cage template.

Clause 10: The system of clause 1, wherein modification of the configuration of the cage template comprises translating the top cage template vertically relative to the bottom cage template and rotating the top cage template relative to the bottom cage template.

Clause 11: The system of clause 1, further comprising means for tracking the configuration of the cage template, wherein a final configuration of the cage template is configured to approximate a cage sized for use in a spinal surgery involving the two vertebra segments.

Clause 12: A method for determining cage sized for use in a spinal surgery involving two vertebra segments, the method comprising: modifying, by a sizing tool, a configuration of a cage template disposed at a distal end of the sizing tool while the cage template is positioned between the two vertebra segments, wherein the modifying is configured to alter a lordotic angle of the cage template, a height of the cage template, or both; measuring, by a plurality of sensors of the cage template, forces applied to the cage template by at least one of two vertebra segments during modification of the configuration of the cage template; outputting, by one or more processors, information associated with the forces applied to the cage template during the modifying; and determining a cage for use in a spinal surgery involving the two vertebra segments based on a final configuration of the cage template, wherein the final configuration of the cage template is based at least in part on the modifying and the information associated with forces applied to the cage template during the modifying.

Clause 13: The method of clause 12, wherein the cage template comprises a top cage template and a bottom cage template, and wherein the plurality of sensors includes at least one sensor associated with the top cage template and at least one sensor associated with the bottom cage template.

Clause 14: The method of clause 13, wherein the lordotic angle of the cage template is modified by rotating the top cage template and the bottom cage template relative to each other.

Clause 15: The method of clause 13, wherein the height of the cage template is modified by via translation in a vertical direction translating the top cage template and the bottom cage template in a vertical direction.

Clause 16: The method of clause 12, further comprising selecting a different cage template in response to determining an optimal configuration of the cage template is not achievable using the cage template, wherein the modifying, measuring, outputting and determining are repeated with the different cage template.

Clause 17: The method of clause 16, wherein the cage template has a first height range and the different cage template has a second height range that is greater than or less than the first height range, the first height range corresponding to range of cage template heights achievable with the cage template via the modifying and the second height range corresponding to range of cage template heights achievable with the different cage template via the modifying.

Clause 18: The method of clause 16, wherein the cage template has a first lordotic angle range and the different cage template has a second lordotic angle range that is greater than or less than the first lordotic angle range, the first lordotic angle range corresponding to range of lordotic angles achievable with the cage template via the modifying and the second lordotic angle range corresponding to range of lordotic angles achievable with the different cage template via the modifying.

Clause 19: A kit for spinal surgery comprising: a cage template comprising: a top cage template; a bottom cage template; a first sensor corresponding to the top cage template; a second sensor corresponding to the bottom cage template; and first and second control supports coupled to the top cage template and the bottom cage template, respectively, wherein a configuration of the cage template is adjustable to alter a height of the cage template, a lordotic angle of the cage template, or both.

Clause 20: The kit of clause 19, further comprising: a sizing tool comprising: an elongated main body having a proximate end and a distal end; and means for transferring a mechanical force to the first and second control supports to modify alter the height of the cage template, the lordotic angle of the cage template, or both while the cage template is disposed between two vertebra segments.

Clause 21: The method of any of clauses 19-20, wherein the first sensor is configured to measure a first force applied to the top cage template by at least one of two vertebra segments during modification of the configuration of the cage template and the second sensor is configured to measure a second force applied to the bottom cage template by at least one of two vertebra segments during modification of the configuration of the cage template.

Clause 22: The method of any of clauses 19-21, further comprising a plurality of cages including cages having different heights, different lordotic angles, or both.

Clause 23: The method of any of clauses 19-22, further comprising one or more additional cage templates.

It should be understood that the present system, kits, apparatuses, and methods are not intended to be limited to the particular forms disclosed. Rather, they are to cover all combinations, modifications, equivalents, and alternatives falling within the scope of the claims.

The claims are not to be interpreted as including means-plus- or step-plus-function limitations, unless such a limitation is explicitly recited in a given claim using the phrase (s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

In the foregoing Detailed Description, various features are grouped together in several embodiments for the purpose of streamlining the disclosure. This method of disclosure is not to be interpreted as reflecting an intention that the disclosed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

Although the embodiments of the present disclosure and their advantages have been described in detail, it should be understood that various changes, substitutions and alterations can be made herein without departing from the spirit and scope of the disclosure as defined by the appended claims. Moreover, the scope of the present disclosure is not intended to be limited to the particular embodiments of the process, machine, manufacture, composition of matter, means, methods and steps described herein. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method, the method comprising:

inserting an adjustable cage template disposed at a distal end of a sizing tool into a spinal cavity between two vertebra segments, the sizing tool being part of a kit that includes one or more cage implants and a plurality of adjustable cage templates, and the plurality of adjustable cage templates have different combinations of lordotic angle ranges and height ranges;

adjusting, by the sizing tool, a configuration of the adjustable cage template, wherein adjusting the configuration of the adjustable cage template is configured to modify a lordotic angle of the adjustable cage template, a height of the adjustable cage template, or both;

selecting a cage implant of the one or more cage implants of the kit based on an adjusted configuration of the adjustable cage template; and replacing the sizing tool and the adjustable cage template with the cage implant based on the adjusted configuration of the adjustable cage template in the same location as the adjustable cage template, wherein the adjusted configuration of the adjustable cage template is based at least in part on the adjusting of the adjustable cage template.

2. The method of claim 1, further comprising:

measuring, by a plurality of sensors of the adjustable cage template, forces applied to the adjustable cage template by at least one of the two vertebra segments, wherein adjusting the configuration of the adjustable cage template is performed based on the forces applied to the adjustable cage template measured by the plurality of sensors of the adjustable cage template to identify a satisfactory configuration of the adjustable cage template.

3. The method of claim 2, wherein measuring the forces applied to the adjustable cage template further comprises:

generating, by the plurality of sensors of the adjustable cage template, sensor data based on the forces applied to the adjustable cage template by the at least one of the two vertebra segments;

sending, by the plurality of sensors of the adjustable cage template, the sensor data to one or more processors; and outputting, by the one or more processors, information associated with the forces applied to the adjustable cage template, wherein the information associated with the forces applied to the adjustable cage template includes pressure data.

4. The method of claim 2, wherein outputting the information associated with the forces further comprises:

transmitting the information associated with the forces applied to the adjustable cage template to a remote device for display.

5. The method of claim 2, wherein at least one sensor of the plurality of sensors of the adjustable cage template is disposed about a peripheral edge of the adjustable cage template.

6. The method of claim 2, wherein at least one sensor of the plurality of sensors of the adjustable cage template is disposed about a central aperture of the adjustable cage template.

7. The method of claim 2, wherein the plurality of sensors of the adjustable cage template are disposed about a peripheral edge and a central aperture of the adjustable cage template.

8. The method of claim 2, wherein the adjustable cage template comprises a top portion and a bottom portion, and wherein the plurality of sensors of the adjustable cage template includes at least one sensor included in the top portion and at least one sensor included in the bottom portion.

9. The method of claim 1, wherein replacing the sizing tool and the adjustable cage template with the cage implant based on the adjusted configuration includes:

removing the sizing tool and the adjustable cage template; and implanting the cage implant based on the adjusted configuration of the adjustable cage template and after the removal of the sizing tool and the adjustable cage template.

10. The method of claim 1, wherein the adjustable cage template is a first adjustable cage template, and the method further comprises, prior to inserting the first adjustable cage template:

inserting a second adjustable cage template in the spinal cavity involving the two vertebra segments;

determining whether a satisfactory configuration of the second adjustable cage template is achievable using the second adjustable cage template; and selecting a different cage template in response to determining that a satisfactory configuration of the second adjustable cage template is not achievable using the second adjustable cage template, wherein the different cage template is the first adjustable cage template.

11. The method of claim 10, wherein the adjustable cage template has a first adjustable height range and the second adjustable cage template has a second adjustable height range;

wherein a first maximum height of the first adjustable height range is greater than a second maximum height of the second adjustable height range; and wherein the determination that a satisfactory configuration of the second adjustable cage template is not achievable is based on insufficient pressure as measured by a second plurality of sensors of the second adjustable cage template when using the second adjustable cage template having the second adjustable height range.

12. The method of claim 10, wherein the adjustable cage template has a first adjustable lordotic angle range and the second adjustable cage template has a second adjustable lordotic angle range;

wherein a first maximum lordotic angle of the first lordotic adjustable angle range is greater than a second maximum lordotic angle of the second adjustable lordotic angle range; and wherein the determining that a satisfactory configuration of the second adjustable cage template is not achievable is based on insufficient pressure as measured by a second plurality of sensors of the second adjustable cage template when using the second adjustable cage template having the second adjustable lordotic angle range.

13. The method of claim 10, wherein the determining whether the satisfactory configuration of the second adjustable cage template is achievable using the second adjustable cage template includes determining an even distribution of compressive forces between the second adjustable cage template and the two vertebra segments.

14. The method of claim 1, further comprising:

obtaining a radiodensity scan of endplates of the two vertebra segments;

determining a Hounsfield Unit score for a region of the endplates of the two vertebra segments based on the radiodensity scan;

determining a Hounsfield Parameter value for the region based on the Hounsfield Unit score for the region and based on a corresponding area of the region, the Hounsfield Parameter value indicative of bone characteristics; and selecting the adjustable cage template from the plurality of adjustable cage templates based on the Hounsfield Parameter value.

15. A method for switching between two adjustable cage templates during a spinal surgery involving two vertebra segments, the method comprising:

inserting a first adjustable cage template disposed at a distal end of a sizing tool into a spinal cavity;

determining whether a satisfactory configuration of the first adjustable cage template is achievable using the first adjustable cage template for implanting a cage implant between the two vertebra segments;

selecting, in response to determining that a satisfactory configuration of the first adjustable cage template is not achievable using the first adjustable cage template, a second adjustable cage template;

removing the first adjustable cage template from the spinal cavity;

inserting the second adjustable cage template into the spinal cavity; and determining whether a satisfactory configuration of the second adjustable cage template is achievable using the second adjustable cage template for implanting the cage implant between the two vertebra segments by:

adjusting a lordotic angle and a height of the second adjustable cage template according to a second adjustable height range and a second adjustable lordotic angle range of the second adjustable cage template; and determining that the satisfactory configuration of the second adjustable cage template is achievable based on sufficient pressure as measured by a second plurality of sensors of the second adjustable cage template when using the second adjustable cage template having the second adjustable height range and the second adjustable lordotic angle range.

16. The method of claim 15, wherein determining whether the satisfactory configuration of the first adjustable cage template is achievable using the first adjustable cage template for implanting a cage implant between the two vertebra segments further comprises:

adjusting a lordotic angle and a height of the first adjustable cage template according to a first adjustable height range and a first adjustable lordotic angle range of the first adjustable cage template; and determining that the satisfactory configuration of the first adjustable cage template is not achievable based on insufficient pressure as measured by a first plurality of sensors of the first adjustable cage template when using the first adjustable cage template having the first adjustable height range and the first adjustable lordotic angle range.

17. A method, the method comprising:

inserting an adjustable cage template disposed at a distal end of a sizing tool into a spinal cavity between two vertebra segments;

adjusting, by the sizing tool, a configuration of the adjustable cage template, wherein adjusting the configuration of the adjustable cage template is configured to modify a lordotic angle of the adjustable cage template, a height of the adjustable cage template, or both;

determining whether an adjusted configuration of the adjustable cage template distributes compressive forces between the two vertebra segments and the adjustable cage template evenly based on sensor data generated by one or more sensors disposed at a peripheral edge of a top surface or a bottom surface of the adjustable cage template;

selecting a matching cage implant from a plurality of cage implants based on the adjusted configuration of the adjustable cage template and responsive to a determination that the adjusted configuration distributes compressive forces between the two vertebra segments and the adjustable cage template evenly;

removing the sizing tool and the adjustable cage template from the spinal cavity; and implanting the selected matching cage implant into the spinal cavity after the removal of the sizing tool and the adjustable cage template.

* * * * *